United States Patent [19]

Kukolja

[11] 4,336,191
[45] Jun. 22, 1982

[54] PENICILLIN CONVERSION BY HALOGEN ELECTROPHILES AND ANTI-BACTERIALS DERIVED THEREBY

[75] Inventor: Stjepan Kukolja, Indianapolis, Ind.

[73] Assignee: Eli Lilly and Company, Indianapolis, Ind.

[21] Appl. No.: 772,086

[22] Filed: Feb. 25, 1977

Related U.S. Application Data

[60] Continuation of Ser. No. 522,539, Nov. 11, 1974, abandoned, which is a division of Ser. No. 273,550, Jul. 20, 1972, Pat. No. 3,860,577, which is a division of Ser. No. 148,129, May 28, 1971, abandoned.

[51] Int. Cl.$^3$ .......................................... C07D 205/08
[52] U.S. Cl. ............................ 260/239 A; 260/245.4
[58] Field of Search ........... 260/239 A, 326 S, 326.27, 260/543 H, 245.4, 239 AL; 544/16

[56] References Cited

U.S. PATENT DOCUMENTS

| | | | |
|---|---|---|---|
| 3,064,042 | 11/1962 | Sernivk | 260/543 H |
| 3,644,458 | 2/1972 | Kampe | 260/239 AL |
| 3,803,224 | 4/1974 | Phillips | 260/543 H |

OTHER PUBLICATIONS

J. M. Steward et al., J. Amer. Chem. Soc. 24, 5880 (1952).
S. Kukolja, J. Amer. Chem. Soc, 93, 6268.
Barton et al., Chem. Comm. 1971, 1137–1139.
Douglass et al., J. Org. Chem. 15, 795 (1950).
Bailar et al., "Comprehensive Chemistry", vol. 2, pp. 858, 1344–1347.
Kharasch et al., "Organic Synthesis", vol. 44, pp. 47–50.

B. Taub, J. Org. Chem. 25, 263–264 (1960).

Primary Examiner—Mark L. Berch
Attorney, Agent, or Firm—William C. Martens; A. R. Whale

[57] ABSTRACT

Novel beta-lactam compounds of the formula

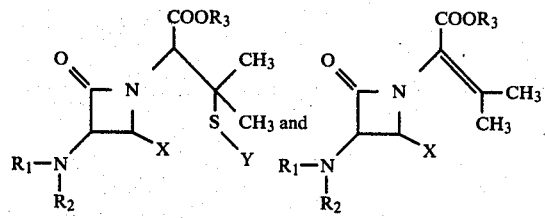

and process for their preparation in which a penicillin ester is reacted with a source of positive halogen to selectively open the thiazolidine nucleus of the penicillin. These compounds are useful as intermediates in the preparation of novel anti-bacterial compounds of the formula:

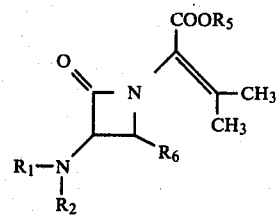

2 Claims, No Drawings

PENICILLIN CONVERSION BY HALOGEN ELECTROPHILES AND ANTI-BACTERIALS DERIVED THEREBY

This is a continuation application of copending application Ser. No. 522,539, filed Nov. 11, 1974, now abandoned, which in turn was a divisional application of the then copending application Ser. No. 273,550, filed July 20, 1972, now U.S. Pat. No. 3,860,577. The latter application was a division of application Ser. No. 148,129, filed May 28, 1971, now abandoned.

This invention relates to a new class of antibacterial agents and intermediates therefor derived from penicillins.

The first of the antibiotics to be discovered were the penicillins, which contain what is now generally referred to as the "penam" nucleus [Sheehan, Heneryl-Logan and Johnson, J.A.C.S., 75, 3292 (footnote 2) (1953)], a thiazolidine ring with a fused beta-lactam. The "penam" nucleus can be represented as follows

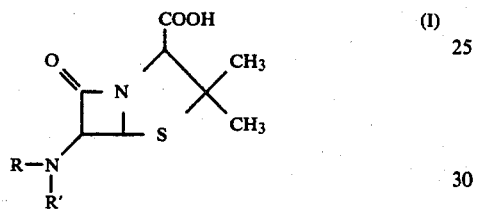

wherein R and/or R' represent hydrogen or a variety of organic radicals, particularly acyl groups as exemplified by hundreds of examples in the prior art. For example, one of the better known penicillins is penicillin V, or phenoxymethyl penicillin, which is known to have the structure

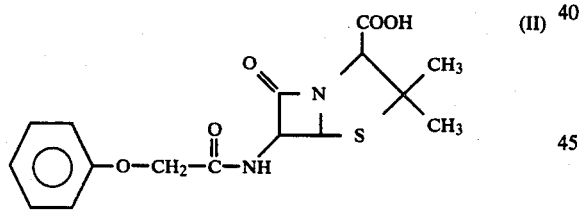

A somewhat more recent discovery is the cephalosporins, a class of antibiotics which are related from the standpoint of chemical structure to the penicillin compounds described. The cephalosporins may be represented by

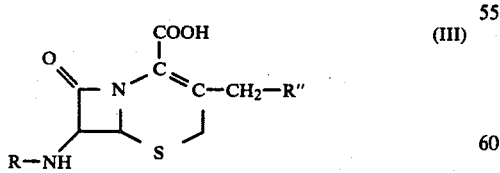

wherein R is preferably an acyl group and R'' can be a number of groups including hydrogen, acetoxy, N-pyridino, etc. as described by the prior art.

It will be seen from the foregoing that both the penicillins and the cephalosporins contain a beta-lactam nucleus. It has therefore been postulated that the beta-lactam nucleus is of considerable importance in providing antibiotic or anti-bacterial activity.

It is known [see Sheehan, "The Synthetic Penicillins" in *Molecular Modification in Drug Design*, pp. 22–23, American Chemical Society (1964)] that the thiazolidine ring of the penicillin nucleus can be opened by the successive use of tertiary butyl hypochlorite and triethyl amine, while leaving the beta-lactam intact. The product can then be hydrogenated to form an azetidinone acetic acid. These reactions can be illustrated by reference to the following:

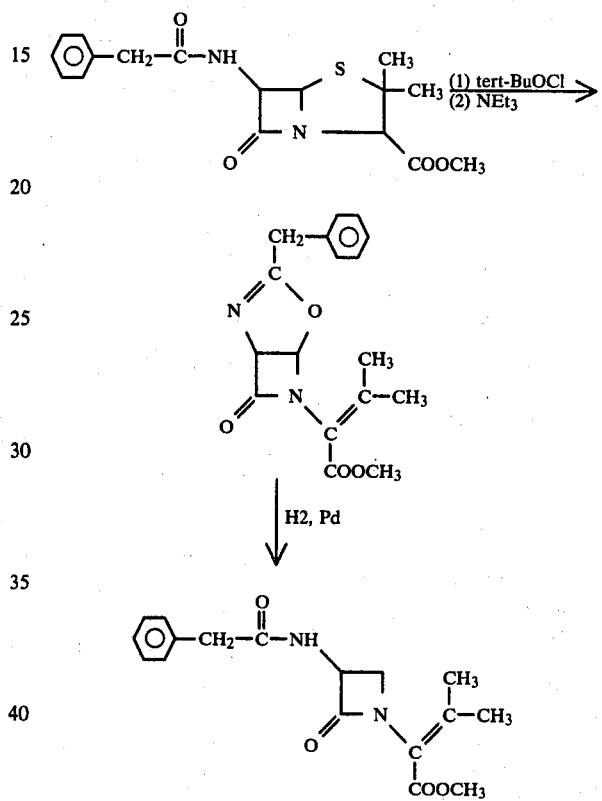

It has now been found that novel intermediates for use in the preparation of novel antibacterials can be produced by selective opening of the thiazolidine ring of penicillin compounds between the sulfur (1-position) and the carbon in the 5-position with electrophiles, while leaving the $\beta$-lactam intact, to form $\beta$-lactam compounds having the following structures:

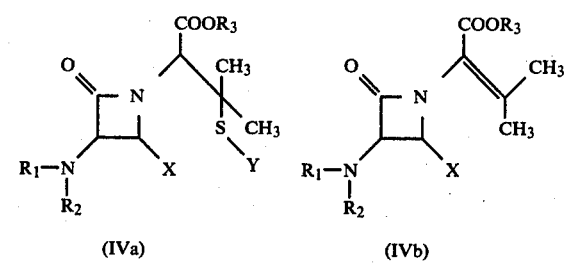

wherein $R_1$ or $R_2$ are hydrogen or an acyl group, or together with the nitrogen atom to which they are bonded define an imido group, $R_3$ is the residue of a carboxy protecting group and X and Y are substituents introduced by electrophilic agents.

It is accordingly an object of the present invention to prepare novel β-lactam compounds of the type described for use as intermediates in the preparation of novel β-lactam derivatives having pharmacological activity.

It is a related object of the invention to provide a process for selective opening of the thiazolidine ring of penicillin compounds while leaving the β-lactam nucleus intact to form the sulfenyl intermediates of this invention.

Another object is to provide a process for selective opening of the thiazolidine ring in penicillin compounds while leaving the β-lactam ring system intact to form the olefinic intermediates.

It is yet another object of the present invention to prepare novel azetidine compounds having antimicrobial activity.

One concept of the present invention resides in a novel class of β-lactam compounds of the following formulas:

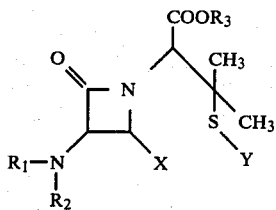 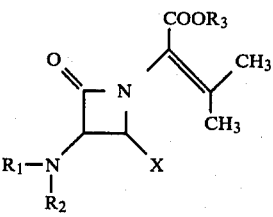

(Va)                    (Vb)

wherein $R_1$ is an acyl group and $R_2$ is hydrogen or $R_1$ and $R_2$, together with the nitrogen atom to which they are bonded define an imido group, $R_3$ is a carboxy protecting group, X is a group including chloro, bromo or alkanoyloxy containing 2 to 6 carbon atoms (e.g., acetoxy, propionoxy, butyryloxy, etc.) and Y is chloro, bromo, or a nitrogen heterocyclic substituent or succinimide.

$R_1$ and/or $R_2$ can be a variety of acyl groups, as exemplified by many of such groups described by the prior art in Behrens et al. U.S. Pat. Nos. 2,479,295, 2,479,297, 2,562,407 and 2,623,876.

Preferred acyl groups include groups of the formula

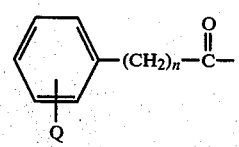

wherein n is zero or an integer from 1 to 5 and Q represents hydrogen or one or more substituents including $C_1$ to $C_3$ alkyl, (e.g., methyl, ethyl, propyl), $C_1$ to $C_3$ alkoxy (e.g., methoxy, ethoxy, propoxy), nitro, halogen (e.g., chlorine, fluorine, bromine and iodine) and trifluoromethyl; groups of the formula

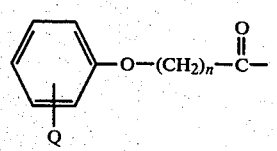

wherein Q and n are as defined above; groups of the formula

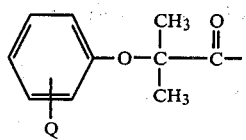

wherein Q is as defined above; and groups of the formula

(VId)

wherein $R_4$ is $C_1$ to $C_6$ alkyl (e.g., methyl, ethyl, propyl, isobutyl, tert-butyl, etc.).

As indicated above, $R_1$ and $R_2$ together with the nitrogen to which they are bonded can define an imido group, and preferably phthalimido. However, $R_1$ and $R_2$ can also define an aliphatic imido group such as a succinimido group.

Representative of acyl groups defined by (VIa) include phenylacetyl, 2,6-dimethoxyphenylacetyl, methylphenylacetyl, p-chlorophenylacetyl, m-trifluoromethylphenylacetyl, o-ethoxyphenylacetyl, p-nitrophenylacetyl, phenylacetyl, phenylpropionyl, as well as a number of others.

Representative of acyl groups encompassed by (VIb) are phenoxyacetyl, p-ethylphenoxypropionyl, 2,6-dimethoxyphenylacetyl, phenoxybutyryl, trifluoromethylphenoxypropionyl, bromophenoxyacetyl, as well as a variety of others. Illustrative of the acyl groups defined by (VIc) include phenoxy-α,α-dimethylacetyl, p-methoxyphenoxy-α,α-dimethylacetyl, etc.

Acyl groups defined by (VId) above include acetyl, propionyl, butyryl, isobutyryl, tert-butylacetyl, etc.

As indicated above, $R_3$ is the residue of an ester-forming alcohol. Since the ultimate product formed from the compounds defined by (Va) and (Vb) above can be in the form of the acid, it is preferred that $R_3$ be an ester residue which is easily cleaved, such as by dilute aqueous base, trifluoroacetic acid or hydrogenation in the presence of a palladium or rhodium catalyst on a suitable carrier such as carbon, barium sulfate or alumina, or by reduction with zinc in an acid such as hydrochloric, acetic or formic acid. A variety of such ester residues are known for this purpose. Preferred groups are those in which $R_3$ is $C_1$ to $C_4$ alkyl such as methyl, n-butyl, tert-butyl, etc., trichloroethyl, benzyl, p-nitrobenzyl, p-methoxybenzyl, benzhydryl, phthalimidomethyl, phenacyl, etc.

Illustrative of compounds of this concept of the invention include the following:

Methyl 2-chloro-α-(1-chlorothio-1-methylethyl)-4-oxo-3-phthalimido-1-azetidineacetate Methyl 2-chloro-α-(1-bromothio-1-methylethyl)-4-oxo-3-phthalimido-1-azetidineacetate 2,2,2-Trichloroethyl 2-chloro-α-(1-chlorothio-1-methylethyl)-4-oxo-3-phthalimido-1-azetidineacetate Benzyl 2-bromo-α-(1-bromothio-1-methylethyl)-4-oxo-3-phthalimido-1-azetidineacetate Benzhydryl 2-chloro-α-(1-chlorothio-1-methylethyl)-4-oxo-3-phenoxyacetamido-1-azetidineacetate 2,2,2-Trichloroethyl 2-chloro-α-(1-chlorothio-1-methylethyl)-4-oxo-3-phenoxy-α,α-dimethylacetamido-1-azetidineacetate
p-Nitrobenzyl 2-chloro-α-(1-chlorothio-1-methylethyl)-4-oxo-3-phenylacetamido-1-azetidineacetate
Methyl 2-chloro-α-(1-chlorothio-1-methylethyl)-4-oxo-3-(2,6-dimethoxyphenyl-acetamido)-1-azetidineacetate
2,2,2-Trichloroethyl 2-bromo-α-(1-bromothio-1-methylethyl)-4-oxo-3-acetamido-1-azetidineacetate
p-Nitrobenzyl 2-chloro-α-(1-chlorothio-1-methylethyl)-4-oxo-3-butyrylamido-1-azetidineacetate
Benzyl 2-chloro-α-(1-chlorothio-1-methylethyl)-4-oxo-3-succinimido-1-azetidineacetate
Benzhydryl 2-chloro-α-(1-chlorothio-1-methylethyl)-4-oxo-3-(3-nitrophenoxypropionamido)-1-azetidineacetate
Methyl 2-bromo-α-(1-bromothio-1-methylethyl)-4-oxo-3-phenylpropionamido-1-azetidineacetate
Methyl 2-acetoxy-α-(1-chlorothio-1-methylethyl)-4-oxo-3-phthalimido-1-azetidineacetate
2,2,2-Trichloroethyl 2-acetoxy-α-(1-bromothio-1-methylethyl)-4-oxo-3-phenoxyacetamido-1-azetidineacetate
p-Nitrobenzyl 2-butyryloxy-α-(1-chlorothio-1-methylethyl)-4-oxo-3-phenylpropionamido-1-azetidineacetate
tert-Butyl 2-propionoxy-α-(1-chlorothio-1-methylethyl)-4-oxo-3-phenoxyacetamido-1-azetidineacetate
Methyl 2-propionoxy-α-(1-chlorothio-1-methylethyl)-4-oxo-3-propionamido-1-azetidineacetate
p-Methoxybenzyl 2-acetoxy-α-(1-bromothio-1-methylethyl)-4-oxo-3-phthalimido-1-azetidineacetate
Methyl 2-chloro-α-isopropylidene-4-oxo-3-phthalimido-1-azetidineacetate
2,2,2-Trichloroethyl 2-chloro-α-isopropylidene-4-oxo-3-phthalimido-1-azetidineacetate
Benzyl 2-bromo-α-isopropylidene-4-oxo-3-phthalimido-1-azetidineacetate
Benzhydryl 2-chloro-α-isopropylidene-4-oxo-3-phenoxyacetamido-1-azetidineacetate
2,2,2-Trichloroethyl 2-chloro-α-isopropylidene-4-oxo-3-phenoxyl-α,α-dimethylacetamido-1-azetidineacetate
p-Nitrobenzyl 2-chloro-α-isopropylidene-4-oxo-3-phenylacetamido-1-azetidineacetate
Methyl 2-chloro-α-isopropylidene-4-oxo-3-(2,6-dimethoxyphenyl-acetamido)-1-azetidineacetate
2,2,2-Trichloroethyl 2-bromo-α-isopropylidene-4-oxo-3-acetamido-1-azetidineacetate
p-Nitrobenzyl 2-chloro-α-isopropylidene-4-oxo-3-butyrylamido-1-azetidineacetate
Benzhydryl 2-chloro-α-isopropylidene-4-oxo-3-(3-nitrophenoxypropionamido)-1-azetidineacetate
Methyl 2-bromo-α-isopropylidene-4-oxo-3-phenylpropionamido-1-azetidineacetate
Methyl 2-acetoxy-α-isopropylidene-4-oxo-3-phthalimido-1-azetidineacetate
2,2,2-Trichloroethyl 2-acetoxy-α-isopropylidene-4-oxo-3-phenoxyacetamido-1-azetidineacetate
p-Nitrobenzyl 2-butyryloxy-α-isopropylidene-4-oxo-3-phenylpropionamido-1-azetidineacetate Another concept of the present invention resides in the opening of the thiazolidine ring of the penicillin nucleus by reaction of a 6-acylamido or 6-imido penicillin ester with an electrophilic reagent. As used herein, the term electrophilic reagent is intended to refer to and include those reagents which seek electrons.

In accordance with the preferred practice of the invention, use is made of an electrophilic reagent which serves as a source of positive halogen to effect selective cleavage or opening of the thiazolidine ring. Without limiting the present invention as to theory, it is believed that the electrophilic reagent attacks the free electron pair on the sulfur atom forming a sulfonium ion which, in turn, causes cleavage in the ring in accordance with the following mechanism.

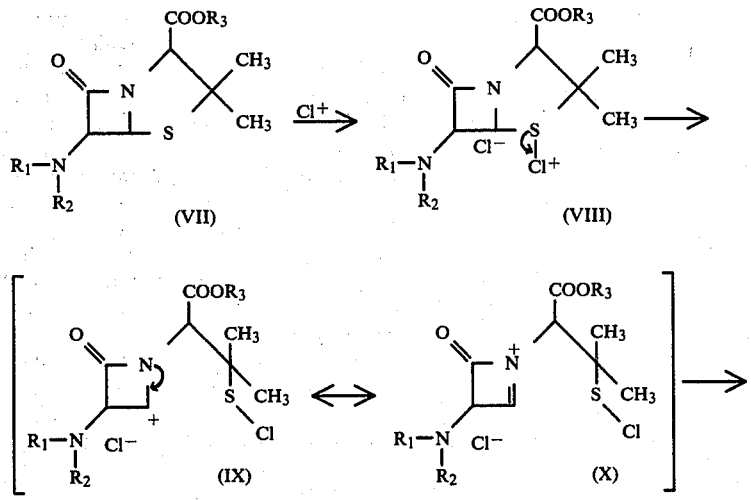

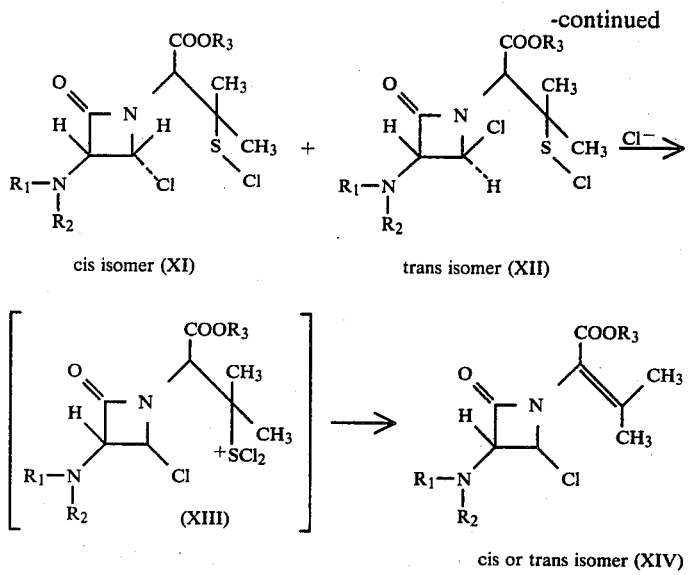

cis isomer (XI)   trans isomer (XII)

(XIII) → cis or trans isomer (XIV)

Thus, as demonstrated by the foregoing, the electrophilic cleavage of the thiazolidine ring results in the formation of a mixture of cis and trans isomers on the 2-carbon atom of the resulting azetidine ring. In the reaction with the second mole of chlorine the sulfur is again attacked with the positive halogen forming a sulfonium ion, which assists the elimination of the β-hydrogen and formation of an olefin group. It will be understood by those skilled in the art that, while the foregoing mechanism has been exemplified using a positive chlorine atom from the electrophilic reagent in the preparation of the novel compounds of this invention, other electrophilic reagents can similarly be employed.

As indicated above, the electrophilic reagent employed in the practice of the process of this invention is preferably formed of an electrophilic component X, a source of positive halogen, and a nucleophilic component Y. As used herein, the term "source of positive halogen" is intended to refer to and include any source of $X_1^+$, wherein $X_1$ is chlorine or bromine. A wide variety of halogenating agents are known to those skilled in the art as supplying positive halogen and can be used in the practice in the invention. Representative of suitable halogenating agents are the elemental halogens, such as chlorine and bromine, sulfuryl chloride, sulfuryl bromide, N-halogeno amides and imides, such as N-chlorosuccinimide, N-bromosuccinimide, N,N'-dibromo hydantoins and organic hypohalite and particularly the alkanoyl hypohalites, such as acetyl hypochlorite, propionyl hypochlorite, butyryl hypochlorite, acetyl hypobromite, propionyl hypobromite, butyryl hypobromite, etc.

In addition, use can also be made of mixed halogen such as BrCl, ClI, BrI, etc. As can be appreciated by those skilled in the art, the use of such mixed halogens provides a product containing mixed halogens.

The compounds described above wherein Y is nitrogen heterocyclic substituents are prepared using N-halo compounds as the source of positive halogen. Use of 1-halo benzotriazole is illustrated below:

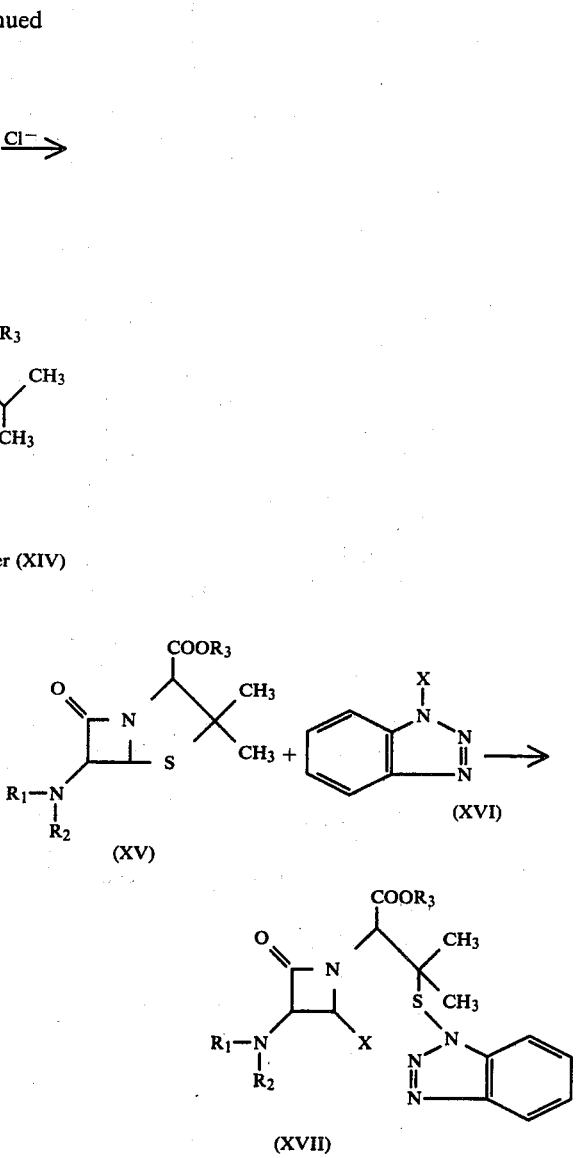

wherein X is Cl or Br.

The reaction described above between the penicillin ester and the source of halogen is preferably carried out in the presence of an aprotic solvent, that is a solvent which does not offer or accept protons. A wide variety of such solvents are known to those skilled in the art and can be used in accordance with the practice of the invention. Representative of suitable solvents which can be used include dimethyl formamide, tetrahydrofuran, dioxane, aliphatic nitriles, such as acetonitrile, propionitrile, etc.; aromatic hydrocarbons and halogenated derivatives, such as benzene, toluene, dichlorobenzene, etc. as well as a number of others. It is frequently preferred to make use of aliphatic halogenated hydrocarbon solvents, such as methylene chloride, chloroform, bromoform, carbon tetrachloride, carbon tetrabromide, ethylene dichloride, ethylene dibromide, etc. since such halogenated solvents have little or no tendency to react with the halogenating agent whereas some of the non-halogenated solvents may not be completely inert, and thus consume halogenating agent.

As will be appreciated by those skilled in the art, the alkanoyl hypohalites can be generated in situ by reaction of halogen with an aliphatic carboxylic acid. In this event, the solvent may be omitted, if desired.

The reaction temperature is not critical to the practice of the process of the invention, and depends somewhat on the nature of the side chain in the 6-position on the penicillin starting material. For example, when use is made of a 6-acylamido penicillin ester, best results are usually obtained with a reaction temperature within the range of −76° C. to 0° C., and with a 6-imido penicillin ester, at a reaction temperature within the range of −76° to 80° C.

The relative proportions between the penicillin ester and the source of positive halogen are important in determining whether the reaction therebetween results in the formation of a compound of the type defined by formula (Va) or of the type defined by formula (Vb). It has been found that when use is made of a mole ratio of source of positive halogen to penicillin ester of up to about 1.5 the predominant product is a compound of the type defined by (Va). When use is made of a mole ratio of source of positive halogen to penicillin ester in excess of about 1.5, and preferably 1.75 to 3.0 or higher, the predominant product is a compound of the type defined by formula (Vb).

As the penicillin ester starting material, use is preferably made of 6-acylamido or 6-imido penicillin esters described above having the formula:

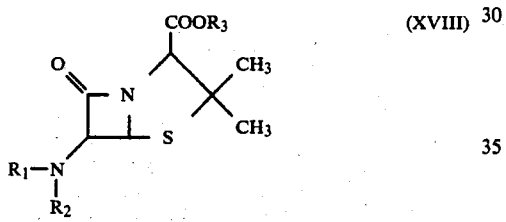

(XVIII)

wherein $R_1$, $R_2$ and $R_3$ are as described above. However, as will be appreciated by those skilled in the art, since $R_1$, $R_2$ and $R_3$ do not enter into the reaction, $R_1$, $R_2$ and $R_3$ can be a number of other groups in addition to those described above.

For convenience, the starting materials for use in the present invention are named by the use of the "penam" nomenclature system described by Sheehan et al., supra. In accordance with this system, "penam" refers to the following saturated ring system:

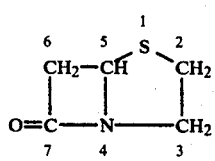

Thus, penicillin V (i.e., phenoxymethyl penicillin) has the structure

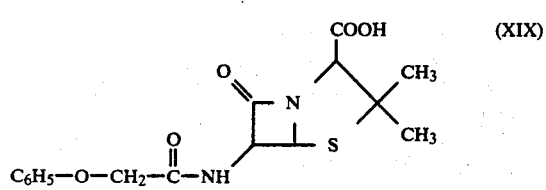

(XIX)

and can be named 6-phenoxyacetamido-2,2-dimethyl-penam-3-carboxylic acid.

Representative penicillin esters which can be used in the process of this invention include the following compounds.

p-Nitrobenzyl 6-phthalimido-2,2-dimethyl-penam-3-carboxylate 2,2,2-Trichloroethyl 6-phthalimido-2,2-dimethyl-penam-3-carboxylate Benzyl 6-succinimido-2,2-dimethyl-penam-3-carboxylate Methyl 6-(diphenoxyacetamido)-2,2-dimethyl-penam-3-carboxylate p-Methoxybenzyl 6-(2′,6′-dimethoxybenzamido)-2,2-dimethyl-penam-3-carboxylate Benzyl 6-(3′-ethylbenzamido)-2,2-dimethyl-penam-3-carboxylate 2,2,2-Trichloroethyl-6-phenoxypropionamido-2,2-dimethyl-penam-3-carboxylate Benzhydryl 6-(3′-trifluoromethylphenylacetamido)-2,2-dimethyl-penam-3-carboxylate Methyl 6-(3′-nitrophenoxybutyrylamido)-2,2-dimethyl-penam-3-carboxylate p-Nitrobenzyl 6-phenylpropionamido-2,2-dimethyl-penam-3-carboxylate Phthalimidomethyl 6-phenoxy-$\alpha,\alpha$-dimethylacetamido-2,2-dimethyl-penam-3-carboxylate Further compounds of this invention (Va) and (Vb) can be used as intermediates in processes for making compounds having antimicrobial activity. Those products have the formula:

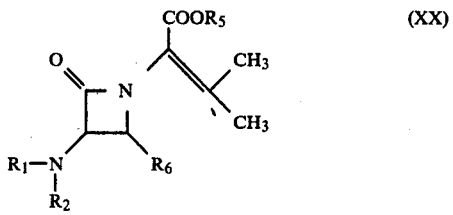

(XX)

wherein $R_1$ and $R_2$ are as described above, $R_5$ can be the residue of an ester group as defined by $R_3$ above but is preferably hydrogen or an alkali metal cation and $R_6$ is a group having the formula $-S-R_7$ where $R_7$ is $C_1$ to $C_5$ alkyl, and preferably isopropyl

(XXI)

It has been found that the foregoing compounds in the form of the acids and metal salts defined by (XX) above have antimicrobial activity, particularly against Gram positive micro-organisms such as Bacillus subtilis and Sarcina lutea. Also see Belgian Pat. No. 754,125, dated Jan. 29, 1971.

The compounds (XX) are derived from the intermediate (Va) and (Vb) described above. For example, the compounds (Va) and (Vb) can be de-esterified in accordance with conventional procedures to yield the corresponding acid.

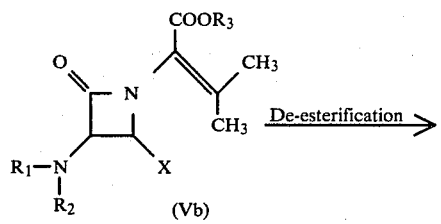

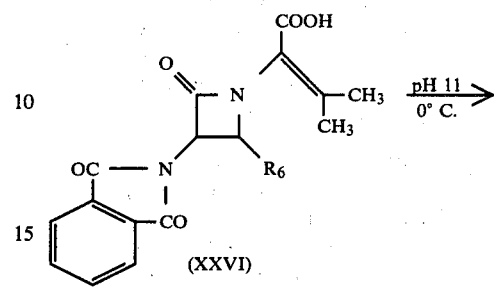

amido by hydrolyzing the imido group with alkali at a pH of around 11 for about 5 minutes at 0° C. This reaction, using the phthalimido group for purposes of illustration, is as follows:

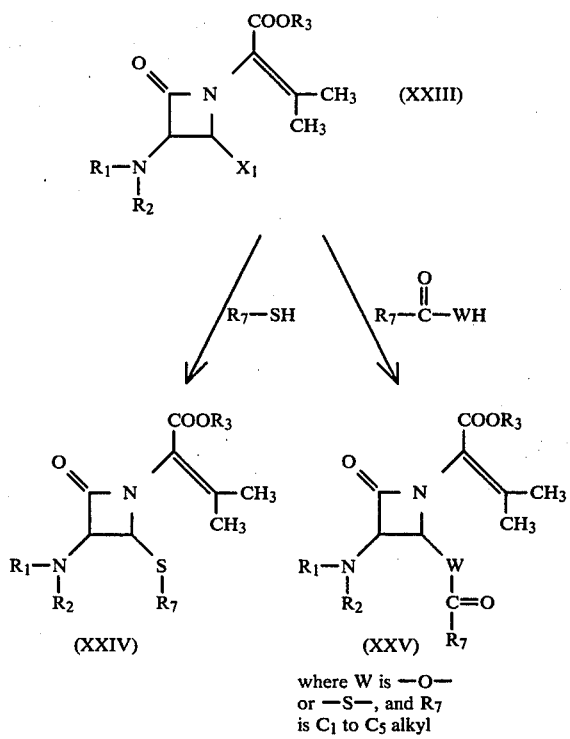

In addition, compounds (Vb) where X is Cl or Br can be reacted with an alkane thiol or disulfide containing 1 to 5 carbon atoms, an alkane carboxylic acid containing 2 to 6 carbon atoms or an alkane thiocarboxylic acid or their derivatives containing 2 to 6 carbon atoms in the presence of reductant (e.g. zinc, etc.) to form the corresponding alkylthio, alkanoyloxy and alkanoylthio derivatives, respectively. These reactions can be illustrated by the following:

where W is —O— or —S—, and $R_7$ is $C_1$ to $C_5$ alkyl

Compounds (XXIV) and (XXV) can then be converted to the corresponding acids in accordance with procedures well known to those in the art.

As indicated above, $R_1$ and $R_2$ in compounds (XX) are as described above, including an imido group when considered together with the nitrogen atom to which they are bonded. It has been found that compounds of the type defined by (XX) where $R_1$ and $R_2$, together with the nitrogen atom to which they are bonded define an imido group, can be converted to the corresponding The resulting phthalamido compounds (XXVII) similarly have antimicrobial activity against Gram positive micro-organisms as described.

Compounds (XX) can also be prepared from the intermediates defined by (Va) by either of two reaction schemes. In accordance with one such scheme, the compounds (Va) are first converted to the corresponding olefinic compound (Vb) by removal of the —S—Y group with a tertiary alkylamine (e.g., triethyl amine, tripropyl amine, tri-isopropyl amine, etc.) as follows:

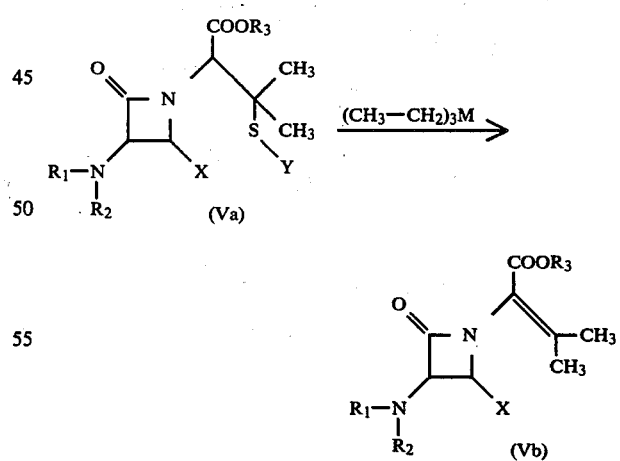

The compounds (Vb) above can then be converted to the desired olefinic acid by the procedures described above.

Alternatively, compounds (Va) can be converted to the corresponding (Vb) compound by treatment with a source of positive halogen of the type described. This reaction may be illustrated as follows:

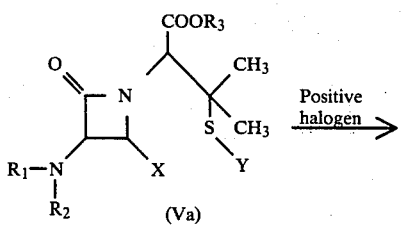

Positive halogen →

(Va)

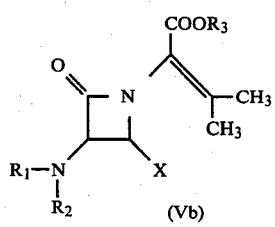

(Vb)

Compounds (Vb) prepared in this manner can also be converted to the desired olefinic acid by the procedures described.

Compounds which can be prepared in accordance with the foregoing concepts include:
- α-isopropylidene-2-isopropylthio-4-oxo-3-phthalimido-1-azetidineacetic acid
- α-isopropylidene-2-isopropylthio-4-oxo-3-succinimido-1-azetidineacetic acid
- α-isopropylidene-2-acetylthio-succinimido-4-oxo-1-azetidineacetic acid
- α-isopropylidene-3-(2'-carboxybenzamido)-4-oxo-2-propionylthio-1-azetidineacetic acid
- α-isopropylidene-2-acetylthio-4-oxo-3-phthalimido-1-azetidineacetic acid
- α-isopropylidene-4-oxo-3-(3'-carboxypropionamido)-2-propionylthio-1-azetidineacetic acid
- α-isopropylidene-2-acetylthio-4-oxo-3-(3'-carboxypropionamido)-1-azetidineacetic acid It will be understood that the present invention also contemplates the esters described above of the foregoing compounds, although the acids and salts are the preferred compounds of this concept of the invention since the latter possess the desired biological activity. The esters, as indicated above, can easily be converted to the corresponding acid or salt in accordance with known procedures.

The compounds of this invention are also useful for making compounds of the formula

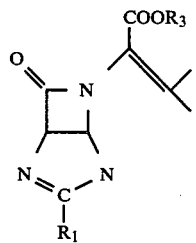

wherein W is —O— or —S— by dehydrohalogenation of the appropriate amide or thioamide with triethylamine. The corresponding thiazoline azetidinones are useful in the synthesis of cephalosporin and penicillin antibiotics by methods described in Cooper application Ser. No. 112,398, now U.S. Pat. No. 3,675,194, and Ser. No. 112,390, now U.S. Pat. No. 3,681,380, both filed Feb. 3, 1971, and antimicrobial thiazoles described in allowed application Ser. No. 832,853, filed June 12, 1969, now U.S. Pat. No. 3,594,389.

In addition to their use as intermediates in the preparation of other compounds of this invention, the compound of (Va) above are also useful as intermediates in the synthesis of other bicyclic β-lactam compounds such as 5-epi-penicillins, which have been found to be useful as inhibitors of β-lactamase, an enzyme which destroys β-lactam antibiotics including, for example, cephalosporin C and cephaloridine (i.e., 7-(2'-thienylacetamido-3-pyridine-methyl-Δ3-cephem-4-carboxylic acid), a relatively new cephalosporin antibiotic disclosed and claimed in U.S. Pat. No. 3,449,338 to Flynn.

By way of example, such 5-epi-penicillins can be prepared by subjecting compounds (Va) to reductive cyclization using, for example, stannous chloride, as illustrated by the following equation:

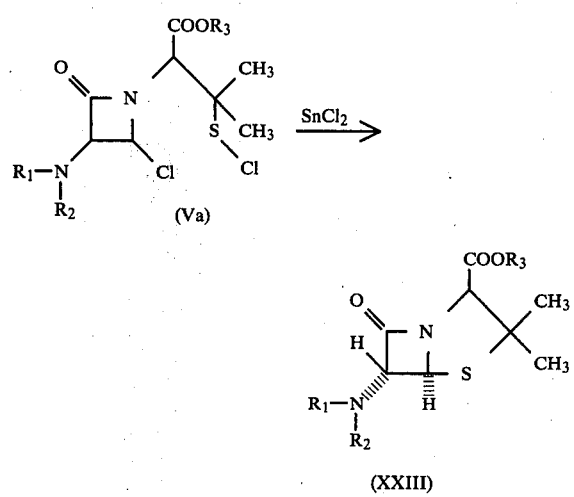

compounds (XXIII) can be converted to the desired acid form by well known procedures to form the desired 5-epi-penicillins.

It has been found that 6-phthalimido-5-epi-penicillanic acid inhibits the activity of β-lactamase on cephaloridine, as demonstrated by a bioassay technique using B.subtilis, K.pneumonias and Mycob. avium. This compound has also been found to inhibit the activity of cephase enzyme on cephalosporin C.

Having described the basic concepts of the invention, reference is now made to the following examples which are provided by way of illustration, and not of limitation, of the practice of the invention.

EXAMPLE 1

This example demonstrates the reaction of methyl 6-phthalimido-2,2-dimethyl-penam-3-carboxylate with sulfuryl chloride.

A mixture of 3.24 g. of methyl 6-phthalimido-2,2-dimethyl-penam-3-carboxylate, 75 ml. of carbon tetrachloride and 0.85 ml. of sulfuryl chloride is refluxed for one hour. Thereafter, the solvent is evaporated, and the residue dissolved in benzene and chromatographed over silica gel using 1600 ml. of benzene and 1600 ml. of a mixture of benzene and ethyl acetate (95:5) as eluting solvents. Fractions of 20 ml. are collected at 15 minute intervals.

Fractions 23 to 28 provide 810 mg. of methyl 2-chloro-α-(1-chlorothio-1-methylethyl)-4-oxo-3- phthalimido-1-azetidineacetate. This material is recrystallized from benzene. mp 158°–160° C.; ir (CHCl$_3$) 1800, 1785, 1750, and 1735 cm$^{-1}$; nmr (CDCl$_3$) 103.5(S, 6H); 232(S,3H); 274.5(S,1H); 332.5 (d,1H,J=2 Hz); 364(d,1H,J=2 Hz) and 471.5 cps (S,4, ArH).

Anal. calcd. for C$_{17}$H$_{16}$Cl$_2$N$_2$O$_5$S: C, 47.34; H, 3.74; Cl, 16.44; N, 6.50; S, 7.43. Found: C, 47.54; H, 4.04; Cl, 16.20; N, 6.29; S, 7.52%.

Fractions 32 to 43 provided 160 mg. of the cis isomer of the above compound, which is recrystallized from benzene; mp 145°–147° C. nmr (CDCl$_3$) 99(S,3H); 103.5(S,3H); 232.5(S,3H); 281(S,1H); 341(d,1H,J=4 Hz); 378.5(d,1H,J=4 Hz) and 472 cps (d,1H,4ArH).

Anal. calcd. for C$_{17}$H$_{16}$Cl$_2$N$_2$O$_5$S: C, 47.34; H, 3.74; Cl, 16.44; N, 6.50; S, 7.43. Found: C, 47.55; H, 3.93; Cl, 16.63; N, 6.31; S, 7.400.

The reaction of this example is repeated using benzene dioxane, tetrahydrofuran and acetonitrile as the solvent, with the same results.

EXAMPLE 2

This example illustrates the reaction of p-nitrobenzyl 6-phthalimido-2,2-dimethyl-penam-3-carboxylate with chlorine.

6-Phthalimido-2,2-dimethyl-penam-3-carboxylic acid p-nitrobenzyl ester is prepared by placing a mixture of 1.0 g. of 6-phthalimido-2,2-dimethyl-penam-3-carboxylic acid, 0.4 ml. of triethylamine, 0.75 g. of p-nitrobenzyl bromide and 10 ml. of dimethyl formamide in a refrigerator for 3 hours. Thereafter, 10 ml. of water are added and the resulting precipitate formed is filtered, washed with acetone and recrystallized from methylethyl ketone to yield colorless crystals; mp 233°–34° C.; nmr (CDCl$_3$) 89(S,3H); 111(S,3H); 287(S,1H); 322(S,2); 338.5(d,1H,J=4.5 Hz); 342(d,1H,J=4.5 Hz); 472 cps (m,8 ArH).

Anal. Calcd. for C$_{23}$H$_{19}$N$_3$O$_7$S: C, 57.38; H, 3.98; N, 8.73; S, 6.60. Found: C, 57.13; H, 4.11; N, 8.53; S, 6.81%.

A solution of 4.81 g.(0.01 mole) of the p-nitrobenzyl ester prepared above in 60 ml. of methylene chloride is cooled with dry ice, and 10 ml.(0.01 mole) of a 1 N solution of chlorine in methylene chloride is added drop-wise over a period of about 10 minutes. The resulting mixture is then maintained at room temperature for 50 minutes, and then the solvent is evaporated and the residue dried in vacuo.

The trans-isomer is isolated as an amorphous solid by chromatography over silica gel and is identified as p-nitrobenzyl 2-chloro-α-(1-chlorothio-1-methylethyl)-4-oxo-3-phthalimido-1-azetidineacetate. ir(CHCl$_3$) 1800, 1785, 1750, 1730, 1400, 1352, and 1108 cm$^{-1}$; nmr (CDCl$_3$) 103.5(S,6); 281(S,1); 328(S,2); 334.5 (d,1,J=2 Hz); 367(d,1,J=2 Hz); and 474 cps (m,8ArH).

Ana. Calcd. for C$_{23}$H$_{19}$Cl$_2$N$_3$O$_7$S: C, 50.01; H, 3.47; Cl, 12.84; N, 7.61; S, 5.81. Found: C, 49.80; H, 3.51; Cl, 12.79; S, 5.74%.

EXAMPLE 3

This example illustrates the reaction of 2,2,2-trichloroethyl-6-phthalimido-2,2-dimethyl-penam-3-carboxylate with sulfuryl chloride.

2,2,2-Trichloroethyl 6-phthalimido-2,2-dimethyl-penam-3-carboxylate is prepared by adding a solution of 11.6 g.(0.06 mole) of 2,2,2-trichloroethylchloroformate in 50 ml. of acetonitrile dropwise over a 15-minute period of a reaction mixture of 17.2 g.(0.05 mole) of 6-phthalimido-2,2-dimethyl-penam-3-carboxylic acid in 100 ml. of dimethyl formamide and 4.8 g.(0.06 mole) of pyridine at room temperature.

The mixture is stirred for one hour, and then poured into 500 g. of ice water. The solid thus formed is filtered and washed with acetone. The creud ester (16.5 g.) is recrystallized from ethyl acetate and again from a mixture of methylene chloride and petroleum ether.

Analytical sample melted at 237°–239°; ir 1824, 1785, 1775 and 1748 cm$^{-1}$; nmr (DMSOd$_6$) 93(s,3H); 106(s,3H); 282(s,1H); 304(s,2H); 339(d,1H,J=4 Hz); 353(d,1H,J=4 Hz); and 476 Hz (s,4 arom.H). Anal. Calcd. for C$_{18}$H$_{15}$Cl$_3$N$_2$O$_5$S: C, 45.25; H, 3.16; Cl, 22.76; N, 5.86; S, 6.71. Found: C, 45.55; H, 3.45; Cl, 22.06; N, 5.95; and S, 6.81%.

A mixture of 47.7 g.(0.1 mole) of the trichloroethyl ester prepared above, 8.5 ml. of sulfuryl chloride and 1 liter of methylene chloride is stirred at room temperature for 90 minutes and then refluxed for 30 minutes. The solvent is then evaporated and the residue dried in vacuo. The product is then chromatographed over 200 g. of silica gel and eluted with 2 l. of benzene, 1 liter of a mixture of benzene and ethyl acetate (95:5) and 2 l. of a mixture of benzene and ethyl acetate (90:10) in accordance with the procedure described in Example 1.

Fractions 6 to 57 yield 24.06 g. of a mixture of the cis and trans isomers (9:1) of 2,2,2-trichloroethyl 2-chloro-α-(1-chlorothio-1-methylethyl)-4-oxo-3-phthalimido-1-azetidineacetate; fractions 58 to 96 provide 1.09 g. of a mixture of the cis and trans isomers (1:1) and fractions 97 to 107 provide 3.05 g. of a mixture of the cis and trans isomers (1:9).

The latter two mixtures of cis and trans isomers (1.09 g. +3.05 g.) are again chromatographed over 100 g. of acid-washed silica gel and eluted with 2 l. of benzene and 2 l. of a mixture of benzene and ethyl acetate (95:5). Fractions (19 ml.) 50–80 gave 0.82 g. of trans isomer; fractions (19 ml.) 81–97 gave 0.22 g. of a mixture of cis and trans (1:9); fractions (19 ml.) 98–114 gave 0.42 g. of cis isomer; fractions (19 ml.) 115–131 gave 0.30 g. of a mixture of cis and trans (1:1); and fractions (19 ml.) 133–183 gave 0.26 g. of a mixture of cis and trans and olefinic compound.

The cis isomer shows nmr (CDCl$_3$) signals at 102 (s, 3H); 107(s,3H); 291 (s,1H); 297(d,2H,J=2 Hz); 342(d,1H,J=4 Hz); 379(d,1H,J=4 Hz); and 472 Hz(d,4 arom. H,J=2.5 Hz). Anal. calcd. for C$_{18}$H$_{15}$Cl$_5$N$_2$O$_5$S: C, 39.41; H, 2.76; Cl, 32.31; N, 5.11; O, 14.58; S, 5.84. Found: C, 39.27; H; 3.02; Cl, 32.56; O, 14.72; and S, 5.68%.

The trans isomer shows nmr (CDCl$_3$) signals at 107(s,6H); 282(s,1H); 296(d,2H,J=1.8 Hz); 334(d,1H,J=1.8 Hz); 472 Hz (d,4 arom. H). Anal. Found: C, 39.14; H, 2.88; Cl, 32.59; O, 14.88 and S, 5.68%.

EXAMPLE 4

The procedure of Example 2 is repeated using benzyl 6-phenoxyacetamido-2,2-dimethyl-penam-3-carboxylate in methylene chloride and chlorine.

The product is identified as benzyl 2-chloro-α-(1-chlorothio-1-methylethyl)-4-oxo-3-phenoxyacetamido-1-azetidineacetate in the form of a mixture of the cis and trans isomers.

EXAMPLE 5

The procedure described in Example 2 is repeated using methyl 6-(2',6'-dimethoxybenzamido)-2,2-dimethyl-penam-3-carboxylate in methylene chloride and bromine.

The product is a mixture of the cis and trans isomers of methyl 2-bromo-α-(1-bromothio-1-methylethyl)-3-(2',6'-dimethoxybenzamido)-4-oxo-1-azetidineacetate.

EXAMPLE 6

This example illustrates the reaction of methyl 6-phenoxyacetamido-2,2-dimethyl-penam-3-carboxylate with sulfuryl chloride.

Methyl 6-phenoxyacetamido-2,2-dimethyl-penam-3-carboxylate (1.82 g.) is dissolved in 25 ml. of carbon tetrachloride and a solution of 0.4 ml. of sulfuryl chloride in 10 ml. of carbon tetrachloride is added. Soon the exothermic reaction is noticed. The mixture is stirred under helium at room temperature for one hour. The solvent is evaporated and the nmr spectrum showed that the product methyl 2-chloro-α-(1-chlorothio-1-methylethyl)-4-oxo-3-phenoxyacetamido-1-azetidineacetate is a mixture of cis- and trans-isomer in a ratio of 1:1.

The cis-isomer shows nmr signals (CDCl$_3$) at 94(s,3H); 99 (s,3H); 238(s,3H); 262(s,1H); 271(s,2H); 342.5(q,1H,J=4 Hz); 370 (d,1H, J=4 Hz), and 420 Hz (m, 5 arom. H).

The trans-isomer shows nmr(CDCl$_3$) signals at 101(s,6H); 238 (s,3H); 274(s,2H); 283(s,1H); 290(q,1H,J=2 Hz); 353(d,1H,J=2 Hz) and 420 Hz(m, 5 arom. H).

EXAMPLE 7

This is an illustration of the reaction between methyl 6-phthalimido-2,2-dimethyl-penam-3-carboxylate with acetyl hypobromite.

A freshly prepared solution of acetyl hypobromite (0.01 mole) is added to a solution of 3.6 g. (0.01 mole) of methyl 6-phthalimido penicillanate in methylene chloride and stirred at room temperature for 1 hour. The solvent was evaporated and the product is a mixture of cis and trans-isomers of methyl 2-acetoxy-α-(1-bromothio-1-methylethyl)-4-oxo-3-phthalimido-1-azetidineacetate.

EXAMPLE 8

The procedure in Example 2 is repeated using p-nitrobenzyl 6-phthalimido-2,2-dimethyl-penam-3-carboxylate and bromine.

The mixture of nitrobenzyl ester and bromine in methylene chloride is stirred for one hour at −76° and one hour at room temperature. After evaporation the product is a mixture of cis- and trans-isomers (ratio 1:1) of p-nitrobenzyl 2-bromo-α-(1-bromothio-1-methylethyl)-4-oxo-3-phthalimido-1-azetidineacetate.

EXAMPLE 9

This example illustrates the reaction of p-nitrobenzyl 6-phthalimido-2,2-dimethyl-penam-3-carboxylate and N-bromosuccinimide.

A mixture of p-nitrobenzyl ester (1 mM), N-bromosuccinimide (3 mM) and a catalytical amount of benzoylperoxide was refluxed for 3 hours in a mixture of methylene chloride and carbon tetrachloride (2:3). The product is identified as a mixture of the cis and trans isomers of p-nitrobenzyl-2-bromo-α-(1-bromothio-1-methylethyl)-4-oxo-3-phthalimido-1-azetidineacetate.

EXAMPLE 10

This example illustrates the reaction between p-nitrobenzyl 6-phthalimido-2,2-dimethyl-penam-3-carboxylate with 1 mole of 1-chlorobenzotriazole.

A reaction mixture of 1 mM of p-nitrobenzyl ester and 1 mM of 1-chlorobenzotrazole in methylene chloride is stirred for 1 hour, the solvent evaporated and the product is trans- p-nitrobenzyl 2-chloro-1(N-benzotriazolylthio-1-methylethyl)-4-oxo-3-phthalimido-1-azetidineacetate.

EXAMPLE 11

This example illustrates the reaction of methyl 6-(phenoxy-α,α-dimethylacetamido)-2,2-dimethyl-penam-3-carboxylate with 1 mole of chlorine.

The starting ester was prepared by reaction of 12 g. of potassium 6-(phenoxy-α,α-dimethylacetamido)-2,2-dimethyl-penam-3-carboxylate with 5 ml. of methyl iodide in 50 ml. of dimethylformamide for 3 hours at room temperature. After usual work-up procedure, the oily residue crystallized by standing at room temperature to give 10 g. of methyl 6-(phenoxy-α,α-dimethylacetamido)-2,2-dimethyl-penam-3-carboxylate.

This ester (392 mg. M) was dissolved in 10 ml. of methylene chloride and a chlorine solution (1 mM) in carbon tetrachloride was added at −76°, stirred for 1 hour, kept at room temperature for 1 hour and evaporated. The nmr spectrum indicates that the product is a mixture of cis and trans isomers (ratio 1:10) of methyl 2-chloro-α-(1-chlorothio-1-methylethyl)-4-oxo-3-(phenoxy-α,α-dimethylacetamido)-1-azetidineacetate.

EXAMPLE 12

The procedure described in Example 1 is repeated using a reaction mixture of benzyl 6-(3'-nitrobenzamido)-2,2-dimethyl-penam-3-carboxylate in carbon tetrachloride and sulfuryl bromide.

The product is identified as a mixture of the cis and trans isomers of benzyl 2-bromo-α-(1-bromothio-1-methylethyl)-3-(3'-nitrobenzamido)-4-oxo-1-azetidineacetate.

EXAMPLE 13

The example illustrates the reaction between N-bromosuccinimide and phthalimidomethyl 6-(4'-trifluoromethylphenoxypropionamido)-2,2-dimethyl-penam-3-carboxylate.

Using the procedure of Example 9, a sample of phthalimidomethyl 6-(4'-trifluoromethylphenoxypropionamido)-2,2-dimethyl-penam-3-carboxylate is dissolved in carbon tetrachloride, and N-bromosuccinimide is added to the resulting solution to provide a mole ratio of the N-bromosuccinimide to ester of about 1.5. The reaction mixture is then refluxed for 2 hours in the presence of a peroxide catalyst, after which the solvent is evaporated.

The residue is dissolved in benzene and chromatographed over silica gel in accordance with the procedure described in Example 1. Fractions containing the cis and trans isomers of phthalimido methyl 2-bromo-α-(1-bromothio-1-methylethyl)-4-oxo-3-(4'-trifluoromethylphenoxypropionamido)-1-azetidineacetate are obtained.

EXAMPLE 14

Using the procedure described in Example 1, phenacyl 6-acetamido-2,2-dimethyl-penam-4-carboxylate is reacted with sulfuryl chloride.

The product is phenacyl 2-chloro-$\alpha$-(1-chlorothio-1-methylethyl)-3-acetamido-4-oxo-1-azetidineacetate.

EXAMPLE 15

The procedure of Example 9 is again repeated using methyl 6-propionamido-2,2-dimethyl-penam-3-carboxylate and N-bromosuccinimide. The product is methyl 2-bromo-$\alpha$-(1-bromo-1-methylethyl)-4-oxo-3-propionamido-1-azetidineacetate.

EXAMPLE 16

This example demonstrates the reaction between methyl 6-phenylpropionamido-2,2-dimethyl-penam-3-carboxylate with acetyl hypochlorite.

A reaction mixture of methyl 6-phenylpropionamido-2,2-dimethyl-penam-3-carboxylate and acetyl hypochlorite in chloroform is stirred at room temperature for 50 minutes. Thereafter, the solvent is evaporated, and the residue is dissolved in benzene and chromatographed over silica gel in accordance with the procedure described in Example 1.

Fractions containing both the cis and trans isomer of methyl 2-acetoxy-$\alpha$-(1-chlorothio-1-methylethyl)-4-oxo-3-phenylpropionamido-1-azetidineacetate are obtained.

The procedure of this example is repeated using chlorine and acetic acid as a solvent for the generation of the hypochloride in situ. The same product is obtained.

EXAMPLE 17

The procedure of Example 7 is repeated using p-nitrobenzyl 6-(4'-methylbenzamido)-2,2-dimethyl-penam-3-carboxylate and propionyl hypobromite.

The product is found to contain both the cis and trans isomers of p-nitrobenzyl 2-propionoxy-$\alpha$-(1-bromothio-1-methylethyl-3-(4'-methylbenzamido)-4-oxo-1-azetidineacetate.

EXAMPLE 18

The procedure described in Example 11 is again repeated using benzhydryl 6-(phenoxy-$\alpha$,$\alpha$-dimethylacetamido)-2,2-dimethylpenam-3-carboxylate and isobutyryl hypochlorite.

The product is identified as benzhydryl 2-isobutyryloxy-$\alpha$-(1-chlorothio-1-methylethyl)-4-oxo-3-phenoxy-6$\alpha$,$\alpha$-dimethylacetamido-azetidineacetate.

EXAMPLE 19

The procedure of Example 7 is again repeated using 2,2,2-trichloroethyl 6-phenoxyacetamido-2,2-dimethyl-penam-3-carboxylate and acetyl hypobromite.

The product is 2,2,2-trichloroethyl 2-acetoxy-$\alpha$-(1-bromothio-1-methylethyl)-4-oxo-3-phenoxyacetamido-1-azetidineacetate.

EXAMPLE 20

The example illustrates the reaction of methyl-6-(2,6-dimethoxyphenylacetamido)-2,2-dimethyl-penam-3-carboxylate with 1 mole of chlorine.

A mixture of 120 g. of sodium 6-(2,6'-dimethoxyphenylacetamido)-2,2-dimethyl-penam-3-carboxylate, 50 ml. of methyl iodide and 503 ml. of dimethylformamide is stirred for 2 hours at room temperature. After work-up, the desired methyl ester is obtained.

A solution of this ester (394 mg.) in 10 ml. of methylene chloride is cooled to $-76°$, the equimolar amount of the chlorine solution added and stirred for 1 hour. Afer evaporation of solvent the nmr spectrum shown that the product is trans isomer of methyl 2-chloro-$\alpha$-(1-chlorothio-1-methylethyl)-4-oxo-3-(2,6-dimethoxyphenylacetamido)-1-azetidineacetate.

EXAMPLE 21

This example illustrates the reaction of methyl 2-chloro-$\alpha$-(1-chlorothio-1-metylethyl)-4-oxo-3-phthalimido-1-azetidineacetate with triethylamine.

To a solution of 1.3 g. of methyl 2-chloro-$\alpha$-(1-chlorothio-1-methylethyl)-4-oxo-3-phthalimido-1-azetidineacetate in 10 ml. of methylene chloride is added a solution of 3 ml. of Et$_3$N in 7 ml. of methylene chloride. The mixture is kept at room temperature for 70 minutes, evaporated to dryness, and the residue extracted with 20 ml. of carbon tetrachloride giving 630 mg. of the crude product. The residue is chromatographed over silica gel using benzene-ethyl acetate (95:5) as the eluting solvent. Fraction containing 10 ml. are collected at 17 minute intervals. Fractions 11–16 give a mixture of a starting material and the desired product. Fractions 17–22 yielded 230 mg. of pure olefinic dimethyl compound as an amorphous solid which is identified as methyl$\alpha$-isopropylidene-2-chloro-4-oxo-3-phthalimido-1-azetidineacetate. nmr (CDCl$_3$) 126.5 (s, 3H); 141 (s, H); 232.5 (s, 3H); 338 (d, 1H, J=2 Hz), 378 (d, 1H, J=2 Hz) and 424.5 Hz (m, 4, Arh).

Anal. calcd. for $C_{17}H_{15}ClN_2O_5$: C, 56.30; H, 4.16; N, 7.72 Cl, 9.77. Found: C, 56.41; H, 4.38; Cl, 9.55; N, 7.95%.

EXAMPLE 22

This example illustrates the preparation of olefinic compounds from penicillin esters.

3.6 g. (0.01 mole) of methyl 6-(phenoxyacetamido)-penicillanate was dissolved in 10 ml. of methylene chloride. While the solution was cooled to $-60°$, 25 ml. of 1 M methylene chloride solution of chlorine was added. The reaction stirred for 30 minutes at $-60°$ and for 30 minutes at room temperature. The solvent was removed in vacuo. The residue is, according to the nmr spectrum (in CDCl$_3$), pure trans isomer and shows signals at 122 and 138.5 (s, 6H, olefinic (CH$_3$)$_2$); 228 (s, Me ester); 274 (q,-OCH$_2$, J=2 and 8 Hz); 311 (q, 1H, J=1.8 and 6 Hz); 444 (m, 5 arom H); and 465 cps (d, NH, J=8.5 Hz).

EXAMPLE 23

This example illustrates the reaction of p-nitrobenzyl 6-phthalimido-2,2-dimethyl-penam-3carboxylate with 2.5 mole of chlorine.

A solution of 7.2 g of above carboxylate in 100 ml. of methylene chloride was cooled to $-60°$ C. and 45 ml. of 1 M solution of chlorine in methylene chloride was added, and stirred for 30 minutes at $-60°$ C. and for 30 minutes at room temperature. The solution was evaporated to dryness to give trans-p-nitrobenzyl $\alpha$-isopropylidene-2-chloro-4-oxo-3-phthalimido-1-azetidineacetate; the nmr spectrum (CDCl$_3$) signals at 129 (s, 3H); 142.5 (s, 3H); 327 (s, 2 N) 338 (d, 1H, J=1.5 Hz); 376 (d, 1H, J=1.5 Hz), and 475 cps (m, 8 arom H).

EXAMPLE 24

Using the procedure described in Example 21, p-nitrobenzyl 2-chloro-α-(1-bromothio-methylethyl)-4-oxo-3-phenoxyacetamido-1-azetidineacetate is reacted with triethyl amine at room temperature for one hour.

The carbon tetrachloride solvent is then removed, and the product separated and identified as p-nitrobenzyl α-isopropylidene-2-chloro-4-oxo-3-phenoxyacetamido-1-azetidineacetate.

EXAMPLE 25

The procedure of Example 21 is again repeated using phenacy 2-acetoxy-α-(1-chlorothio-1-methylethyl)-4-oxo-3-propionamido-1-azetidineacetate. After removal of the phenacyl group, the product is α-isopropylidene-2-acetoxy-4-oxo-3-propionamido-1-azetidineacetic acid.

EXAMPLE 26

The procedure of Example 22 is repeated using bromine and tert-butyl 6-acetamido-2,2-dimethyl-penam-4-carboxylate in a mole ratio of 2.3.

The solvent is removed from the reaction mixture, and the product recovered in accordance with the procedure described. After removal of the tert-butyl group, the product is identified as α-isopropylidene-3-acetamido-2-bromo-4-oxo-1-azetidineacetic acid.

EXAMPLE 27

The procedure of Example 22 is again repeated using sulfuryl chloride and benzyl 6-phenoxy-α,α-dimethylacetamido-2,2-dimethyl-penam-4-carboxylate in a mole ratio of 2.5.

The product is identified as benzyl -isopropylidene-2-chloro-4-oxo-3-phenoxy-α,α-dimethylacetamido-1-azetidineacetate.

EXAMPLE 28

The procedure of Example 7 is again repeated using acetyl hypochlorite and methyl 6-benzamido-2,2-dimethyl-penam-4-carboxylate in a mole ratio of 3.0. The product is identified as methyl α-isopropylidene-2-acetoxy-3-benzamido-4-oxo-1-azetidineacetate.

EXAMPLE 29

The procedure described in Example 10 is repeated except that the mole ratio of N-chlorobenzotraizole to the penicillin ester is 3.0. The product is p-nitrobenzyl α-isopropylidene-2-chloro-4oxo-3-phthalimido-1-azetidineacetate.

EXAMPLE 30

This example illustrates the preparation of trans-2,2,2-trichloroethyl α-isopropylidene-2-chloro-4-oxo-3-phthalimido-1-azetidineacetate.

A solution of 27.2 g. of trans-2,2,2-trichloroethyl 2-chloro-α-(1-chlorothio-1-methylethyl)-4-oxo-3-phthalimido-1-azetidineacetate in 200 ml. of methylene chloride is cooled to $-76°$ and 100 ml. of 1 M carbon tetrachloride solution of chlorine is added. The mixture is stirred for 2 hours at $-76°$, for 1 hour at room temperature, and the evaporated to dryness, giving the named product as a colorless, amorphous solid: ir (CHCl$_3$); 1800, 1782, 1735, 1396 and 1109 cm$^{-1}$; nmr (CDCl$_3$) 130 (s, 3H); 146 (s, 3H); 296 (q, 2H, J=8 and 12 Hz); 336 (d, 1H, J=1.8 Hz); 372 (d, 1H, J=1.8 Hz) and 472 cps (m, 4H).

Anal. calcd. for $C_{18}H_{14}Cl_4N_2O_5$: C, 45.03; H, 2.94; Cl, 29.54; N, 5.83; O, 16.66. Found: C, 45.14; H, 3.09; Cl, 29.71; N, 5.54; and O, 16.59%.

EXAMPLE 31

This example illustrates the preparation of 2,2,2-trichloroethyl α-isopropylidene-2-isopropylthio-4-oxo-3-phthalimido-1-azetidineacetate and the corresponding acid.

A mixture of 4.8 g. of trans-2,2,2-trichloroethyl α-isopropylidene-2-chloro-4-oxo-3-phthalimido-1-acetidineacetate, 2.4 g. of zinc dust, and 48 ml. of isopropyl mercaptan is refluxed for 75 minutes, cooled, and the insoluble zinc salts removed by filtration. The filtrate is acidified and extracted with ethyl acetate. The acetate phase is separated and filtrate evaporated. The remaining solid is dissolved in 50 ml. of ethyl acetate and re-extracted with sat. solution of sodium bicarbonate, the ethyl acetate extract is washed with water, dried, (MgSO$_4$) and evaporated to yield 3.89 g. of a neutral fraction which is chromatographed over 100 g. of silica gel and eluted with 1 l. of benzene, 2 l. of benzene; ethyl acetate (95:5), 1 l. benzene: ethyl acetate (90:10). Fractions 83-103 give 0.12 g. of a mixture of cis and trans esters and fractions 104-121 give 0.78 g. of 2,2,2-trichloroethyl α-isopropylidene-2-isopropylthio-4-oxo-3-phthalimido-1-azetidine-acetate: nmr(CDCl$_3$) 72(s, 3H); 78(s,3H); 131(s, 3H); 178(m, 1H); 296(q, 2H, J=8 and 12); 321(d, 1H, J=2 Hz); 338 (d, 1H, J=2 Hz); and 472 cps(m, 4H).

Anal calcd. for: $C_{21}H_{21}Cl_3N_2O_5S$: C, 48.53; H, 4.07; Cl, 20.46; N, 5.39; O, 15.39; S, 6.17. Found: C, 48.36; H, 4.23; Cl, 20.54; N, 5.62; O, 15.48; and S, 6.40%.

The acidified filtrate and sodium bicarbonate washing are combined, reacidified with conc. HCl(pH 2.5), and extracted yielding 1.09 g. of a mixture of cis and trans acids. The mixture is dissolved in 3.0 ml. of acetone and left at room temp. overnight giving 100 mg. of colorless silky needles of cis-α-isopropylidene-2-isopropylthio-4-oxo-3-phthalimido-1-azetidineacetic acid: ir(CHCl$_3$) 1782, 1774, 1736, 1728 and 1396 cm$^{-1}$; nmr(CDCl$_3$) 67(d, H, J=3.5 Hz); 74(d, 3H, J=3.5 Hz); 145(s, 6H); 170(m, 1H); 332(d, 1H, J=4.6 Hz); 347(d, 1H, J=4.6 Hz); 472 Hz(m, 4H), and 515 cps(b,1H); p$K_a$=6.1(66% DMF).

Anal. calcd for: $C_{20}H_{20}N_2O_5S$: C, 58.75; H, 5.19; N, 7.21 O, 20.59; S, 8.25. Found: C, 59.03; H, 5.18; N, 7.23, O, 20.30 and S, 8.35.

EXAMPLE 32

This example illustrates the reaction of methyl α-isopropylidene-2-chloro-4-oxo-3-phthalimido-1-azetidineacetate with isopropyl disulfide and zinc in acetic acid.

A mixture of 1.0 g. of trans-methyl α-isopropylidene-2-chloro-4-oxo-3-phthalimido-1-azetidineacetate, 3 g. of zinc dust, 7 ml. of isopropyl disulfide and 20 ml. of acetic acid are stirred for 5 hours, filtered and the filtrate evaporated. The residue was dissolved in ethylacetate and the solution washed with water, a sodium bicarbonate solution, water, and dried (MgSO$_4$). The nmr spectrum of the crude product shows 4 components: cis and trans-2-isopropylthio- and cis and trans-2-acetoxy azetidine derivatives. The mixture is separated by chromatography over silica gel.

The cis isomer of methyl α-isopropylidene-2-isopropylthio-4-oxo-3-phthalimido-1-azetidineacetate showed nmr(CDCl$_3$) signals centered at 68 (q, 6H); 139.5(s, 6H);

175(m, 1H); 228(s, 3H); 325(d, 1H, J=4 Hz); 342(d, 1H, J=4 Hz), and 471 cps (m, 4 arom. H).

The corresponding trans isomer shows nmr(CDCl$_3$) at 70(s, 3H) 77(s, 3H); 126(s, 3H); 138(s, 3H); 175(m, 1H); 230(s, 3H); 320(d, 1H, J=2 Hz); 332(d, 1H, J=2 Hz); and 471 cps(m, 4 arom. H).

The trans isomer of methyl α-isopropylidene-2-acetoxy-4-oxo-3-phthalimido-1-azetidine acetate shows nmr(CDCl$_3$) at 127 (s, 6H); 138(s, 3H); 231(s, 3H); 324(d, 1H, J=2 Hz); 393(d, 1H, J=2 Hz) and 471 cps(m, 4 arom H).

EXAMPLE 33

This example illustrates the preparation of α-3-(2'-carboxybenzamido)-2-isopropylthio-4-oxo-1-azetidineacetic acid.

A solution of 200 mg. of α-isopropylidene-2-isopropylthio-4-oxo-3-phthalimido-1-azetidineacetic acid dissolved in 3 ml. of acetone is cooled in an ice water bath and 1 N solution hydroxide solution is added slowly to maintain the pH at 11. After stirring for 5 minutes the solution is acidified to pH3 with 1 N HCl and extracted twice with ethyl acetate. The extract is washed with water, dried (MgSO$_4$) and evaporated in vacuo. A thin layer chromatography, developed with chloroform: acetic acid (9:1) using silica gel plate, indicates a very slow-moving polar diacid. The bioautographs (*Bacillus subtilis* and *Sarcina lutea*) show active spots. The nmr spectrum is consistent with a diacid structure. The product shows Gram-positive biological activity by the disc-diffusion method.

It will be understood that various changes and modifications may be made in the details of procedure, formulation and use without departing from the spirit of the invention, especially as defined in the following claims.

I claim:

1. A method for selectively opening the S, —C$_5$ bond of the thiazolidine ring of a compound selected from the group consisting of a 6-acylamido penicillin ester and a 6-imido penicillin ester comprising reacting the penicillin ester with an alkanoyl hypohalite in an aprotic solvent.

2. A method as defined in claim 1 wherein the alkanoyl hypohalite is generated in situ by reaction of halogen with an aliphatic carboxylic acid.

* * * * *